US008298817B2

(12) United States Patent
Nakayama et al.

(10) Patent No.: US 8,298,817 B2
(45) Date of Patent: Oct. 30, 2012

(54) VECTOR

(75) Inventors: Yasuhide Nakayama, Toyonaka (JP); Makoto Nagaishi, Kobe (JP); Mariko Shiba, Suita (JP)

(73) Assignees: National Cerebral and Cardiovascular Center, Osaka (JP); Bridgestone Corporation, Tokyo (JP)

( * ) Notice: Subject to any disclaimer, the term of this patent is extended or adjusted under 35 U.S.C. 154(b) by 575 days.

(21) Appl. No.: 11/252,063

(22) Filed: Oct. 18, 2005

(65) Prior Publication Data

US 2006/0057714 A1 Mar. 16, 2006

Related U.S. Application Data

(63) Continuation of application No. PCT/JP2004/005450, filed on Apr. 16, 2004.

(30) Foreign Application Priority Data

Apr. 18, 2003 (JP) ................................ 2003-114541

(51) Int. Cl.
*C12N 15/00* (2006.01)
*A61K 47/48* (2006.01)
*C08G 63/48* (2006.01)
*C08G 63/91* (2006.01)

(52) U.S. Cl. .................................... 435/320.1; 525/54.2

(58) Field of Classification Search ........................ None
See application file for complete search history.

(56) References Cited

U.S. PATENT DOCUMENTS

| | | | | |
|---|---|---|---|---|
| 4,558,120 | A | 12/1985 | Tomalia et al. | |
| 5,610,268 | A * | 3/1997 | Meijer et al. | 528/363 |
| 5,830,948 | A | 11/1998 | Frechet et al. | |
| 5,919,422 | A * | 7/1999 | Yamanaka et al. | 422/121 |
| 5,985,573 | A * | 11/1999 | Hennink et al. | 435/6.12 |
| 6,127,481 | A * | 10/2000 | Janssen et al. | 525/106 |
| 6,846,809 | B2 * | 1/2005 | Cristiano et al. | 514/44 R |
| 7,153,252 | B2 * | 12/2006 | Luscher | 483/62 |
| 7,795,031 | B2 * | 9/2010 | Demeneix et al. | 435/455 |
| 2003/0026840 | A1 | 2/2003 | Plank et al. | |
| 2003/0236207 | A1 * | 12/2003 | Debin et al. | 514/44 |

FOREIGN PATENT DOCUMENTS

| | | | |
|---|---|---|---|
| JP | 2000-509428 | A | 7/2000 |
| JP | 2003-500469 | A1 | 1/2003 |
| WO | 9524221 | A1 | 9/1995 |
| WO | 9706201 | A1 | 2/1997 |
| WO | 98/28357 | A1 | 7/1998 |
| WO | WO 99/06055 | A1 | 2/1999 |
| WO | WO 9906055 | A1 * | 2/1999 |
| WO | 01/00708 | A1 | 1/2001 |
| WO | 00/73263 | A1 | 7/2002 |
| WO | 2004014951 | A3 | 2/2004 |
| WO | WO 2004/011527 | A1 | 2/2004 |

OTHER PUBLICATIONS

V. Toncheva et al, "Novel vectors for gene delivery formed by self-assembly of DNA with poly(L-lysine) grafted with hydrophilic polymers", *Biochimica et Biophysica Acta*, vol. 1380, No. 3, 1998, pp. 354-368.

Y.H. Choi et al., "Lactose-Poly(ethylene Glycol)-Grafted Poly-L-Lysine as Hepatoma Cell-Targeted Gene Carrier", *Bioconjugate Chem.*, vol. 9, 1998, pp. 708-718.

S. Han et al., "Water-Soluble Lipopolymer for Gene Delivery", *Bioconjugate Chem.*, vol. 12, 2001, pp. 337-345.

M. Umeda et al., "Hikari Cation Seisei-gata Shinsuisei Kobunshi o Mochiita DNA tono Complex Keisei no Hikari seigyo", *Polymer Preprints*, Japan, vol. 51, No. 5, May 10, 2002, p. 976.

Tang M X et al., The influence of polymer structure on the interactions of cationic polymers with DNA and morphology of the resulting complexes, Gene Therapy, 1997, pp. 823-832 vol. 4, No. 8.

Petersen Holger et al., Star-shaped poly(ethylene glycol)-block-polyethylenimine copolymers enhance DNA condensation of low molecular weight polyethylenimines, Biomacromolecules, Sep. 2002, pp. 926-936, vol. 3, No. 5.

Wetering Van De P et al., Relation between transfection efficiency and cytotoxicity of poly(2- (dimethylamino)ethyimethacrylate)/ plasmid complexes, Journal of Controlled Release, Nov. 10, 1997, pp. 59-69 vol. 49, No. 1, Elsevier, Amsterdam, NL.

Nakayama et al., High performance gene delivery polymeric vector: nano-structured cationic star polymers(star vectors) Current Drug Delivery, Bentham Science Publishers, Jan. 1, 2005, vol. 2, No. 1, pp. 53-57, Hilversum, NL.

Ranganathan D et al: Design and Synthesis of $AB^3$-Type (A=1,3,5-Benzenetricarbonyl unit; B=GLU DIOME or $GLU^7$ Octa OME) Peptide Dendrimers: Crystal structure of the First Generation, Biopolymers, Jan. 1, 2000, vol. 54, No. 4, pp. 289-295, New York, NY, US.

Appelhans D et al.,: Synthesis and Characterization of poly(ether amide) dendrimers containing different core molecules, Macromolecules, ACS, Jan. 1, 2000, vol. 33, pp. 9494-9593, Washington, DC, US.

Fujii H et al., Antimetastatic Activities of Synthetic arg-gly-asp-ser (RGDS) and arg-leu-asp-ser (RLDS) Peptide Analogues and their Inhibitory Mechanisms, Biological & Pharmaceutical Bulletin (of Japan), Pharmaceutical Society of Japan, Dec. 1, 1995, vol. 18, No. 12, pp. 1681-1688, Tokyo, JP.

Kwock E W et al: The convergent Synthesis of Four Generations of Monodisperse Aryl Ester Dendrimers, Polymer Preprints, American Chemical Society, Jan. 1, 1991, vol. 32, No. 3, pp. 635-636, US.

Tomalia D A et al., Starburst Dendrimers: Molecular-level control of Size, Shape, Surface, Chemistry, Topology, and Flexibility from Atoms to Macroscopic Matter, Angewandte Chemie, International Edition, Wiley VCH, Feb. 1, 1990, vol. 29, No. 2, pp. 138-175, Verlag, Weinheim.

(Continued)

*Primary Examiner* — Robert M Kelly
(74) *Attorney, Agent, or Firm* — Sughrue Mion, PLLC

(57) ABSTRACT

The present invention provides a vector which can make nucleic acids to be an aggregate and locate a vector containing a cationic polymer to surround the aggregate so as to protect the nucleic acids from the enzyme. The vector comprises a polymer having branched chain(s). Preferably, 3, 4, or 6 branched chains are bonded to benzene ring. It is preferable that the number of the branched chains is higher. As the branched chain(s), a vinyl-series acrylic polymer is preferable. The vector is synthesized by reacting a dithiocarbamate compound with an acrylamide monomer for the branched chain(s).

7 Claims, 7 Drawing Sheets

OTHER PUBLICATIONS

Nakayama Y et al., Development of high-performance gene delivery vector: Photocontrol of DNA complex formation, International Journal of Artificial Organs, Aug. 31, 2002, vol. 25, No. 7, p. 723, Milan, IT.

Hayashi M et al, High performance Gene Delivery Polymeric Vector: Molecular Design of Photo-Cation Generatable Water-Soluble Polymers, International Journal of Artificial Organs, Sep. 6, 2003, vol. 26, No. 7, p. 3.

* cited by examiner

VECTOR

CROSS REFERENCE TO RELATED APPLICATION

This is a continuation Application of PCT/JP2004/005450 filed on Apr. 16, 2004. The entire disclosure of the prior application is hereby incorporated by reference.

FIELD OF THE INVENTION

The present invention relates to a vector on gene transfection technology.

BACKGROUND OF THE INVENTION

As the molecular genetic factors on human disorders became clearer, study for gene therapy has been increasingly emphasized recently. Gene therapy is intended to express DNA on targeted regions. The important things for gene therapy are how to deliver the DNA to the targeted region, and how to effectively introduce the DNA into the targeted region and express functionally the DNA on the region. As a vector for introducing foreign DNA, many viruses including retrovirus, adenovirus, and herpesvirus, which are altered to transfer therapeutic gene, have been used for clinical trials on human gene therapy. However, the risks of infection and immune reaction still remain.

As a non-viral vector for transferring DNA into cells, for example, dioleoyloxypropyl trimethylammonium, which is a cationic lipid (Felgner et al., Proc. Natl. Acad. Sci. USA, 84, 7413-7417, 1987), has been commercialized as Lipofectin (registered trademark). As a synthetic polymer for vector, polyethyleneimine has been commercialized as Exogen.

DNA-lipid complexes are described in Felgner et al., PNAS, 84 (1987) 7413.

Generally, nucleic acids are not stable within a living body and are decomposed by a certain type of enzyme.

SUMMARY OF THE INVENTION

The present invention provides a vector which can make nucleic acids to be an aggregate and locate a vector containing a cationic polymer to surround the aggregate so as to protect the nucleic acids from the enzyme.

The vector of the present invention comprises a cationic polymer having branched chain(s).

The vector of the present invention forms a complex with the aggregate of nucleic acids and can be administered into a living body.

As a device for insertion into living body, there are devices to be percutaneously inserted into tissues near diseased parts and devices to be placed within blood vessels such as a blood vessel catheter and a stent graft. However, the device is not limited thereto.

Generally, nucleic acids are not stable in living body and are decomposed by a certain type of enzyme. A nucleic-acid-containing complex using the vector of the present invention can make nucleic acids to be an aggregate and locate a vector containing a cationic polymer to surround the aggregate so as to protect the nucleic acids from the enzyme, thereby making at least nucleic acids inside the aggregate to operate normally in the living body. In addition, the nucleic-acid-containing complex can be enclosed in a micro- or nano-order sized capsule or micelle and thus can be administered into a blood vessel.

PREFERRED EMBODIMENTS OF THE INVENTION

Figure 1:
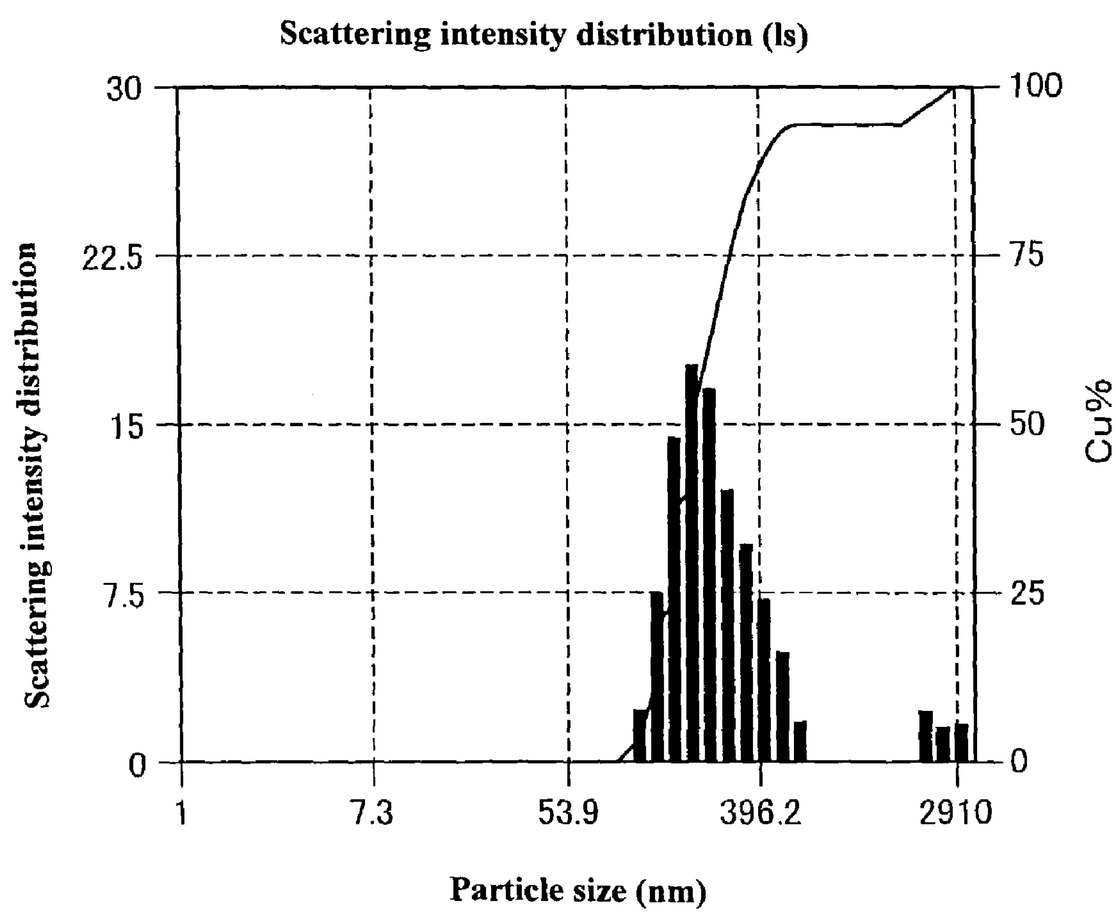
FIG. 1 is a graph showing measurement results of the particle distribution of a polyion complex.

Cationic polymer employed in the present invention has branched chain(s).

In an aspect of the present invention, the effect of vector is enhanced within a certain molecular weight range. The range depends on the number of the branched chain(s).

In an aspect of the present invention, a vector has three polymer chains and a molecular weight (number average molecular weight) of from 30,000 to 60,000.

In an aspect of the present invention, a vector has four polymer chains and a molecular weight of from 30,000 to 65,000.

In an aspect of the present invention, a vector has six polymer chains and a molecular weight of from 10,000 to 50,000.

In an aspect of the present invention, a vector includes nonionic groups which are bonded to ends of the branched chains of the polymer.

In an aspect of the present invention, the vector is composed of a polymer which comprises a polyfunctional compound as its nucleus, a plurality of polymer chains as the branched chains which are bonded to the nucleus, and nonionic groups which are bonded to the ends of the polymer chains. The nonionic groups may be aromatic compounds, aliphatic compounds, polyacrylic esters, or polymethacrylic esters.

In a preferred embodiment of the present invention, a plurality of branched chains are bonded to a polyfunctional compound, preferably benzene ring, naphthalene, anthracene, or pyrene. In the case of benzene ring, the number of bonds is from 2 to 6, especially 2, 3, 4, or 6. The larger the number of bonds, the more effective it is. In the case of naphthalene, the number of bonds can be up to 8. In the case of anthracene or pyrene, the number of bonds can be up to 10. In addition, biphenyl (in this case, the number of bonds of branched chains can also be up to 10) in which a plurality of aromatic rings in noncoplanar relation are bonded or a cycloparaffin hydrocarbon such as cyclohexane may be employed as the nucleus.

As the nucleus to which the branched chains are bonded, benzene ring is preferable. Specific examples are as follows. An example for three branched chains is 2,4,6-tris (N,N-diethyldithiocarbamylmethyl) mesitylene which is obtained by addition reaction between 2,4,6-tris (bromomethyl) mesitylene and sodium N,N-diethyldithiocarbamate in ethanol. An examples for four branched chains is 1,2,4,5-tetrakis (N,N-diethyldithiocarbamylmethyl) benzene which is obtained by an addition reaction between 1,2,4,5-tetrakis (bromomethyl) benzene and sodium N,N-diethyldithiocarbamate in ethanol. An example for six branched chains is hexakis (N,N-diethyldithiocarbamylmethyl) benzene which is obtained by an addition reaction between hexakis (bromomethyl) benzene and sodium N,N-diethyldithiocarbamate in ethanol.

As for the branched chain, homopolymer or copolymer of vinyl series monomer is preferable. The length of each branched chain may be either the same or different. The structure of the chain may be either linear straight-chain structure or dendritic branched-chain structure. When the branched chain is a homopolymer, specifically, a polymer of 3-N,N-dimethylaminopropyl acrylamide, $CH_2{=}CHCONHC_3H_6N(CH_3)_2$, is preferable.

By mixing the 3-N,N-dimethylaminopropyl acrylamide and the aforementioned each benzene derivative with an alcohol solution such as methanol or a solution of low polarity solvent such as chloroform in consideration of the solubility and subjecting the mixture to photopolymerization reaction, a cationic polymer in which the aforementioned polymer of vinyl series monomer is bonded to the benzene ring via $—CH_2—$ derived from the aforementioned benzene derivative is produced. The molecular weight of the thus produced vector is preferably from 5,000 to 500,000, especially 5,000 to 100,000, particularly 10,000 to 50,000. In addition, when the branched chain is a copolymer, it may be either a random copolymer or a block copolymer. If it includes a cationic functional monomer as the monomer, a copolymer of a nonionic monomer or a hydrophobic monomer may be employed. As the nonionic monomer, nonionic hydrophilic monomers such as N,N-dimethylacrylamide, N-vinylpyrrolidone, and PEG-(meth) acrylate are preferable. As the hydrophobic monomer, ethyl (meth) acrylate and styrene are preferable. The vector composed of thus produced cationic polymer surrounds the nucleic acids and functions as a nucleic-acid-containing complex, thereby inhibiting the deactivation and decomposition of the nucleic acids due to enzyme within a living body.

The polymer chain composing the branched chain may be a polymer chain which has a quaternary amine on its proximal end and a tertiary amine on its distal end. When quaternary amine is placed near the nucleus to which the branched chain is bonded and tertiary amine is placed around the quaternary amine, reduction of cytotoxicity and high efficiency of gene transfection could be expected. Quaternary amine is cation which is an essential ingredient of a vector. However, quaternary amine has cytotoxicity as it is used as a fungicide or an antibacterial coating. Therefore, placing tertiary amine around the quaternary amine would be of great advantage in cytotoxicity. As a matter of course, besides the combination of quaternary and tertiary, combinations of such as quaternary and primary, quaternary and secondary, tertiary and primary, tertiary and secondary may be possible.

Moreover, the cationic polymer within the vector of the present invention may have such a nature that the positive charge thereof is deactivated with time. Since the positive charge within the vector is deactivated as mentioned above, the function of emission of the nucleic acids from the nucleic acid aggregate which is surrounded by the vector can be given. The conditions may be set by a person skilled in the art in such a manner that the emission of nucleic acids will be conducted after the vector permeates the cell membrane. The cationic polymer having such function may be a polymer carrying a compound having 4,4'-benzylidenebis (N,N-dimethylaniline) skeleton on its branched chains of a long-chain form. The compounds having 4,4'-benzylidenebis (N,N-dimethylaniline) skeleton may be leucomalachite green. The cationic polymer carrying the aforementioned compounds is converted to cation by light irradiation, and has a nature that the positive charge thereof is deactivated with time.

To combine the vector composed of cationic polymer and the nucleic acids, the nucleic acids are added to and mixed with dispersion liquid in which the concentration of the vector is from about 1 to about 1,000 μg/mL at room temperature. It is preferable to add the cationic polymer to the nucleic acids in an excessive amount so as to make a nucleic-acid-containing complex in which the cationic polymer is combined with the nucleic acid in the saturated state of the cationic polymer.

As the nucleic acid, polynucleotide such as deoxyribonucleic acid (DNA) and ribonucleic acid (RNA) are preferable. Among these, DNA is especially preferable. The nucleic acid may be ribonucleoprotein.

The nucleic acid may be herpes simple virus thymidine kinase gene (HSV1-TK gene), p53 tumor suppressor gene, and BRCA1 tumor suppressor gene, cytokine gene such as TNF-α gene, IL-2 gene, IL-4 gene, HLA-B7/IL-2 gene, HLA-B7/B2M gene, IL-7 gene, GM-CSF gene, IFN-γ gene and IL-12 gene, or cancer antigen peptide gene such as MART-1 and MAGE-1. These are available for cancer therapy.

Moreover, cytokine gene such as VEGF gene, HGF gene, and FGF gene, c-myc antisense, c-myb antisense, cdc2 kinase antisense, PCNA antisense, E2F decoy, and p21 (sdi-1) gene are available for blood vessel disease treatment. These genes are well known to those skilled in the art.

The particle size of the nucleic-acid-containing complex is preferably from about 50 to about 400 nm. If it is smaller than this range, there is possibility that the effect of the enzyme affects the nucleic acids in the nucleic-acid-containing complex and there is also possibility that the nucleic-acid-containing complex is filtered out at the kidney. Moreover, if it is larger than this range, there is possibility that the nucleic-acid-containing complex has difficulty in introduction into cells.

Nucleic acid is used in a form that it can exhibit its function within cells by the introduction into the cells. For instance, in the case of DNA, nucleic acid is used in the form of plasmid in which the DNA is transcribed within cells where the nucleic acid is introduced and is arranged such that the DNA can exhibit its function through production of polypeptide to be encoded. Preferably, promoter region, initiation codon, DNA which codes protein having desired function, termination codon, and termination region are seriated.

If required, two or more kinds of nucleic acids may be included in a single plasmid.

According to the present invention, "cells" preferable for introduction of nucleic acid are cells which allow the nucleic acid to exhibit its function and are selected diversely according to the nucleic acid to be used (i.e., the function thereof). Examples of such cells include cardiac muscle cell, smooth muscle cell, fibrocyte, skeletal muscle cell, vascular endothelial cell, bone marrow cell, bone forming cell, hematocyte stem cell, blood cell, tumor cell, hemopoietic stem cell, peripheral stem cell, SP cell, ES cell, B cell, T cell, NK cell. Moreover, the examples also include gastrointestinal tract epithelial cells and renal tubular epithelial cells such as monocyte, dendritic cell, macrophage, histiocyte, Kuppfer cell, osteoclast, synovial A cell, microgliocyte, Langerhans cell, epithelioid cell, multinucleate giant cell.

Nucleic-acid-containing complex using the vector of the present invention can be administered in any given manner.

As for the administration, intravenous or intraarterial infusion is especially preferable. However, the nucleic-acid containing complex may be administered into muscle, into adipose tissues, under the skin, intradermally, into lymphatic vessels, into lymph nodes, into body cavities (pericardial cavity, pleural cavity, abdominal cavity, cerebrospinal cavity, and the like), and into bone marrow. Besides these, the nucleic-acid containing complex may be administered directly into diseased tissues, for example, spraying alveolus with the nucleic-acid containing complex by using a tracheal endoscope.

Drugs of which active ingredient is the nucleic-acid-containing complex can be further mixed with carrier (osmotic adjuster, stabilizer, preservative, solubilizer, pH adjuster, thickener, and the like) acceptable in pharmaceutical preparations if necessary. These carriers may be of heretofore known type. Moreover, an indirect manner which is well known to those skilled in the art and in which the nucleic-acid-containing complex is used outside the body first and then administered into a living body may be employed. For instance, the indirect manner comprises letting the nucleic-acid-containing complex affect cells taken from the living body such as lymph cells having high tumor cytotoxicity to give drug sensitive to the cells and, after that, administrating them into the living body after incubation. In this case, it is possible to injure the tumor cells with the lymph cells incubated, and kill the administered lymph cells by drugs if any side effect is confirmed.

Moreover, drugs of which active ingredient is the nucleic-acid-containing complex include drugs containing two or more kinds of nucleic-acid-containing complexes of which nucleic acids are different from each other. Drugs having several therapeutic purposes as mentioned above are especially helpful in the field of the diversifying gene therapys.

As for the administration quantity of such drug, the quantity to animal, especially the quantity to human, depends on various factors such as the targeted nucleic acids, the administration manner, and the particular part to be treated. However, the administration quantity should be sufficient enough to cause remedial response.

The nucleic-acid-containing complex therein is preferably applied for gene therapy. The applicable diseases depend on the kind of the nucleic acids contained in the complex. Specific examples include peripheral arterial disease, coronary artery disease, and diseases which are caused at circulatory organ region after arterial dilatation such as restenosis. The examples also include cancers (malignant melanoma, brain tumor, metastasizing malignancy, breast cancer, and the like), infection diseases (such as HIV), and monogenic disorders (cystic fibrosis, chronic granulomatous disease, alpha-1-antitrypsin deficiency, Gaucher's disease, and the like).

EXAMPLES

Example 1

Synthesis of Single Branched Chain Type Vector

First, benzyl N,N-diethyldithiocarbamate was synthesized according to the following reaction formula (Formula 1).

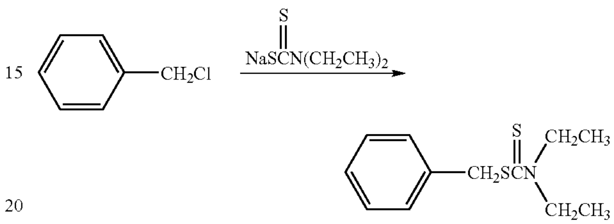

benzyl N,N-diethyldithiocarbamate

More specifically, 10 ml of ethanol solution containing benzyl chloride (4.8 g, 38 mmol, Mw. 126.58) was added dropwise into 50 ml of ethanol solution containing sodium N,N-diethyldithiocarbamate trihydrate (10.3 g, 46 mmol, Mw. 225.31) in nitrogen atmosphere at 0° C. After agitating the reaction solution for 23 hours at room temperature, 150 ml of water was added and extracted by diethylether (200 ml×3 times). The organic layer was washed with water (100 ml×3 times) and was dried by sodium sulfate. Solvent was distilled away under reduced pressure using an evaporator so as to obtain benzyl N,N-diethyldithiocarbamate (colorless liquid). Yield point was 17.6 g (yield: 93%), $^1$H-NMR: δ7.407 ppm to 7.271 ppm (m, 5H, Ar—H), δ4.540 ppm (s, 2H, Ar—$CH_2$S), δ4.082 ppm to 4.012 ppm (q, 2H, —N—$CH_2$—), δ3.763 ppm to 3.692 ppm (q, 2H, —N—$CH_2$—), δ1.311 to 1.252 ppm (m, 6H, —$CH_2$—$CH_3$).

Then, using the benzyl N,N-diethyldithiocarbamate thus obtained, dimethylaminopropyl acrylamide was polymerized according to the following reaction formula (Formula 2).

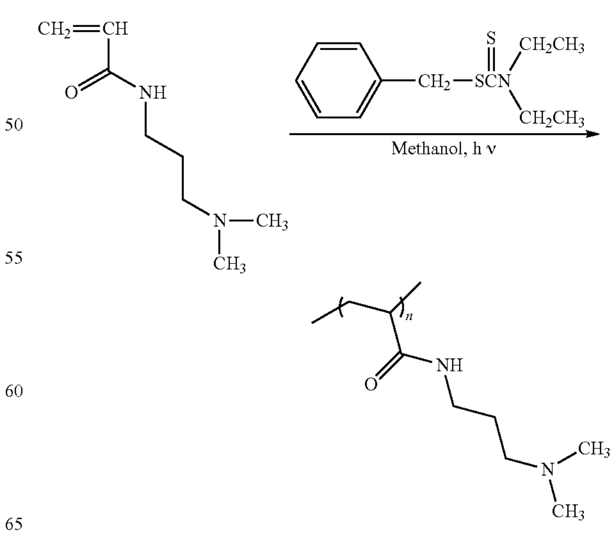

More specifically, a mixture of dimethylaminopropyl acrylamide (3.9 g, 24.96 mmol, Mw. 156.23) and benzyl N,N-diethyldithiocarbamate (23.94 mg, 0.1 mmol, Mw. 239.41) was diluted with methanol so as to prepare solution of 20 mL in total. The solution thus prepared was agitated while nitrogen gas was blown in, and was irradiated with ultraviolet light (light intensity 1 $mW/cm^2$). After 30 minutes of ultraviolet irradiation, polymer solution was concentrated using an evaporator and was added dropwise to a large quantity of diethylether so as to precipitate high-molecular-weight polymer. Supernatant liquid was removed by decantation and the high-molecular-weight polymer was dissolved in water and was freeze-dried. Molecular weight of the high-molecular-weight polymer was measured after freeze-dried, and was approximately 18,000, $^1$H-NMR: δ7.8 ppm to 7.4 ppm (br, 1H, —NH), δ3.43 ppm to 3.0 ppm (br, 2H, —NH—$CH_2$—$CH_2$—), δ2.4 ppm to 2.2 ppm (br, 2H, —$CH_2$—$CH_2$—$NR_2$), δ2.2 ppm to 2.1 ppm (br, 6H, —N—$CH_3$), δ1.8 ppm to 1.5 ppm (br, 2H, —$CH_2$—$CH_2$—$CH_2$—).

Example 2

Synthesis of 3 Branched Chain Type Vector

Next, 2,4,6-tris (N,N-diethyldithiocarbamylmethyl) mesitylene was synthesized by reacting sodium N,N-diethyldithiocarbamate with 2,4,6-tris (bromomethyl) mesitylene according to the following reaction formula (Formula 3).

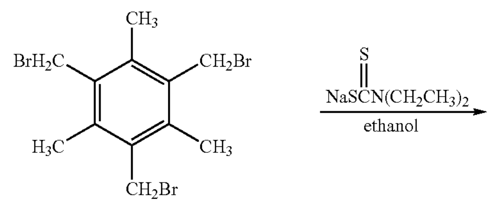

-continued

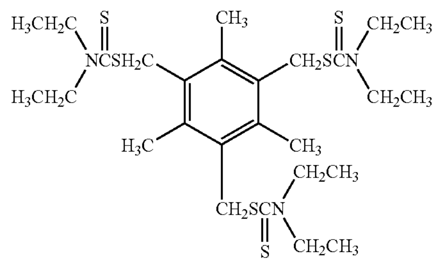

2,4,6-tris (N,N-diethyldithiocarbamylmethyl) mesitylene

More specifically, ethanol (100 ml) and sodium N,N-diethyldithiocarbamate trihydrate (5.43 g, 24.12 mmol, Mw. 225.31) were added to 2,4,6-tris (bromomethyl) mesitylene (2 g, 4.02 mmol, Mw. 398.98) and were agitated at room temperature. After 24 hours from the start of the agitation, the mixture was filtered and the precipitate was collected. The collected precipitate was dissolved in chloroform, and was washed with water using a separatory funnel. Thus formed chloroform layer was concentrated using an evaporator and vacuum-dried using a desiccator, thereby obtaining 2,4,6-tris (N,N-diethyldithiocarbamylmethyl) mesitylene (white solid). Yield point was 3.03 g (yield: 98.4%), $^1$H-NMR: δ4.447 ppm (s, 6H, Ar—$CH_2$S), δ4.086 ppm to 4.015 ppm (q, 6H, —N—$CH_2$—), δ3.746 ppm to 3.676 ppm (q, 6H, —N—$CH_2$—), δ2.421 ppm (s, 9H, Ar—$CH_3$), δ1.324 ppm to 1.222 ppm (m, 18H, —$CH_2$—$CH_3$).

To 2,4,6-tris (N,N-diethyldithiocarbamylmethyl) mesitylene thus obtained, dimethylaminopropyl acrylamide was polymerized according to the following reaction formula (Formula 4), thereby synthesizing a three branched chain type vector.

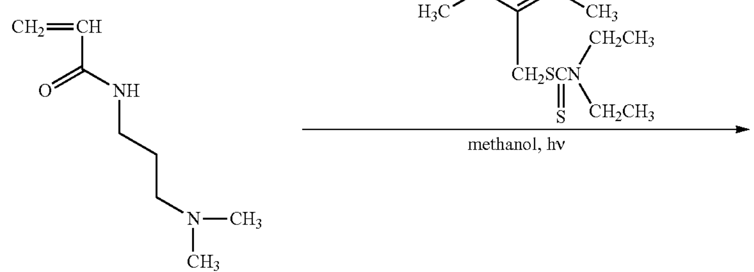

-continued

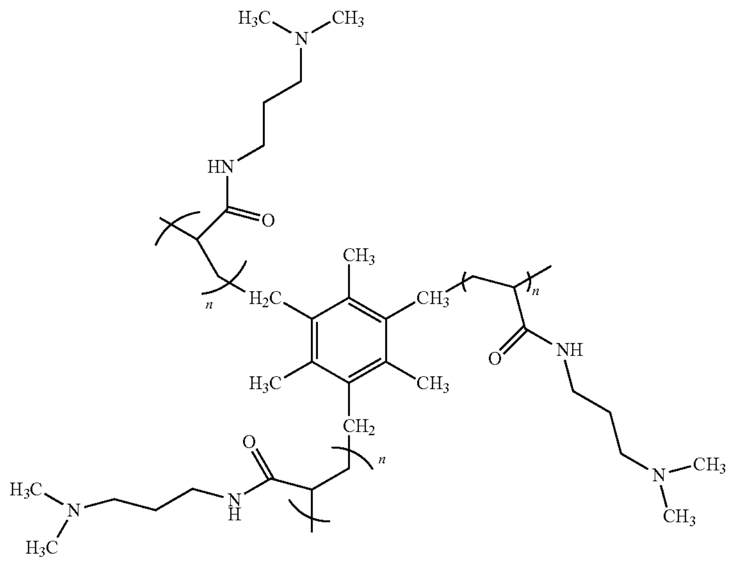

More specifically, 2,4,6-tris (N,N-diethyldithiocarbamylmethyl) mesitylene (20.14 mg, 1.67 mmol, Mw. 604.08) was dissolved in chloroform (300 μl) and was added to methylaminopropylacrylamide (1.6224 g, 10.38 mmol, Mw. 156.23). The mixture was diluted with methanol to prepare solution of 20 ml in total. The solution thus prepared was agitated while nitrogen gas was blown in, and was irradiated with ultraviolet light (light intensity 1 $mW/cm^2$). After 30 minutes of ultraviolet irradiation, polymer solution was concentrated using an evaporator and was added dropwise to a large quantity of diethylether to precipitate the high-molecular-weight polymer. Supernatant liquid was removed by decantation and high-molecular-weight polymer was dissolved in water and was freeze-dried. Molecular weight of the obtained high-molecular-weight polymer was measured using a GPC after freeze-dried and was approximately 18,000. In addition, $^1$H-NMR: δ7.7 ppm to 7.4 ppm (br, 1H, —NH), δ3.4 ppm to 3.0 ppm (br, 2H, —NH—$CH_2$—$CH_2$—), δ2.4 ppm to 2.3 ppm (br, 2H, —$CH_2$—$CH_2$—$NR_2$), δ2.3 ppm to 2.1 ppm (br, 6H, —N—$CH_3$), δ1.8 ppm to 1.5 ppm (br, 2H, —$CH_2$—$CH_2$—$CH_2$—).

Example 3

Synthesis of Four Branched Chain Type Vector

First, 1,2,4,5-tetrakis (N,N-dithiocarbamylmethyl) benzene was synthesized according to the following reaction formula (Formula 5).

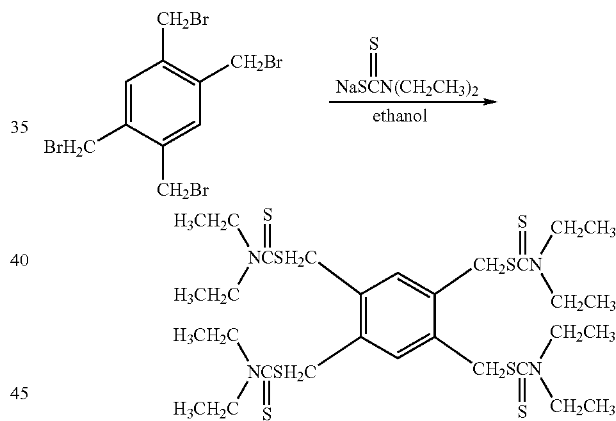

1,2,4,5-tetrakis (N,N-dithiocarbamylmethyl)

More specifically, ethanol (100 mL) and sodium N,N-diethyldithiocarbamate trihydrate (4 g, 17.76 mmol, Mw. 225.31) were added to 1,2,4,5-tetrakis (bromomethyl) benzene (1 g, 2.22 mmol, Mw. 449.83) and were agitated at room temperature. After 48 hours from the start of agitation, the mixture was filtered and the precipitate was collected. The collected precipitate was dissolved in chloroform, and was washed with water using a separatory funnel. The chloroform layer was concentrated using an evaporator and was vacuum-dried using a desiccator, thereby obtaining 1,2,4,5-tetrakis (N,N-dithiocarbamylmethyl) benzene (white solid). Yield point was 1.48 g (yield: 91.4%). Measurement of $^1$H-NMR resulted in δ7.487 ppm (s, 2H, Ar—H), δ4.573 ppm (s, 8H, Ar—$CH_2$S), δ4.065 ppm to 3.994 ppm (q, 8H, —N—$CH_2$—), δ3.765 ppm to 3.687 ppm (q, 8H, —N—$CH_2$—), δ1.304 ppm to 1.256 ppm (t, 24H, —$CH_2$—$CH_3$).

To 1,2,4,5-tetrakis (N,N-diethyldithiocarbamylmethyl) benzene thus obtained, dimethylaminopropyl acrylamide was polymerized according to the following reaction formula (Formula 6), thereby synthesizing a four branched chain type vector.

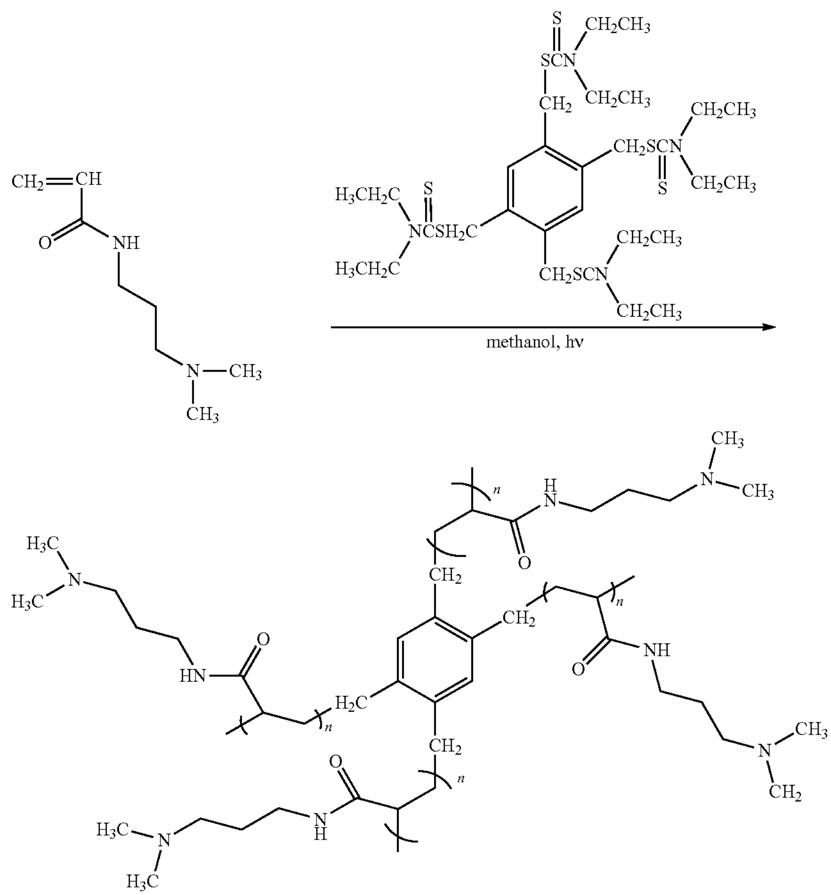

More specifically, 1,2,4,5-tetrakis (N,N-diethyldithiocarbamylmethyl) benzene (18.08 mg, 1.25 mmol, Mw. 723.30) was dissolved in chloroform (300 μl) and was added to dimethylaminopropyl acrylamide (1.326 g, 8.49 mmol, Mw. 156.23). The mixture was diluted with methanol so as to prepare solution of 20 ml in total. The solution thus prepared was agitated while nitrogen gas was blown in, and was irradiated with ultraviolet light (light intensity 1 $mW/cm^2$). After 30 minutes of ultraviolet irradiation, polymer solution was concentrated using an evaporator and was added dropwise to a large quantity of diethylether to precipitate the high-molecular-weight polymer. Supernatant liquid was removed by decantation and high-molecular-weight polymer was dissolved in water and was freeze-dried. Molecular weight was measured using a GPC after freeze-dried, and was approximately 18,000. In addition, $^1$H-NMR: δ7.8 to 7.4 ppm (br, 1H, —NH), δ3.4 ppm to 3.0 ppm (br, 2H, —NH—$CH_2$—$CH_2$—), δ2.4 ppm to 2.2 ppm (br, 2H, —$CH_2$—$CH_2$—$NR_2$), δ2.2 ppm to 2.1 ppm (br, 6H, —N—$CH_3$), δ1.8 ppm to 1.5 ppm (br, 2H, —$CH_2$—$CH_2$—$CH_2$—).

Example 4

Synthesis of Six Branched Chain Type Vector

First, hexakis (N,N-diethyldithiocarbamylmethyl) benzene was synthesized according to the following reaction formula (Formula 7).

hexakis (N,N-diethyldithiocarbamylmethyl) benzene

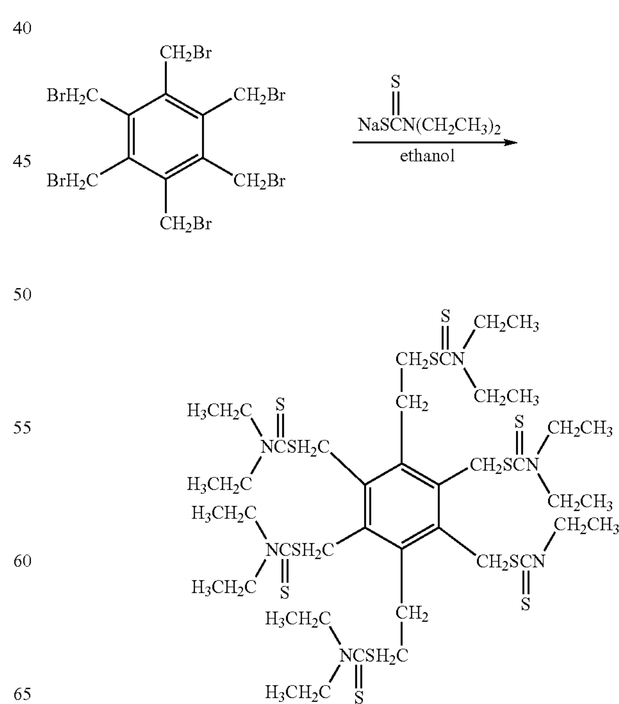

More specifically, ethanol (200 ml) and sodium N,N-diethyldithiocarbamate trihydrate (6.36 g, 28.23 mmol, Mw. 225.31) were added to hexakis (bromomethyl) benzene (1 g, 1.57 mmol, Mw. 635.68) and were agitated at room temperature. After 4 days from the start of agitation, the mixture was filtered and the precipitate was collected. The collected precipitate was dissolved in chloroform, and was washed with water using a separatory funnel. The chloroform layer was concentrated using an evaporator and was vacuum-dried using a desiccator, thereby obtaining hexakis (N,N-diethyldithiocarbamylmethyl) benzene (white solid). Yield point was 1.48 g (yield: 90.2%). $^1$H-NMR: δ4.565 ppm (s, 12H, Ar—$CH_2$S), δ4.012 to 3.988 ppm (q, 12H, —N—$CH_2$—), δ3.731 ppm to 3.708 ppm (q, 12H, —N—$CH_2$—), δ1.307 ppm to 1.261 ppm (m, 36H, —$CH_2$—$CH_3$).

Then, dimethylaminopropyl acrylamide was polymerized to the hexakis (N,N-diethyldithiocarbamylmethyl) benzene thus obtained according to the following reaction formula (Formula 8), thereby synthesizing a six branched chain type vector.

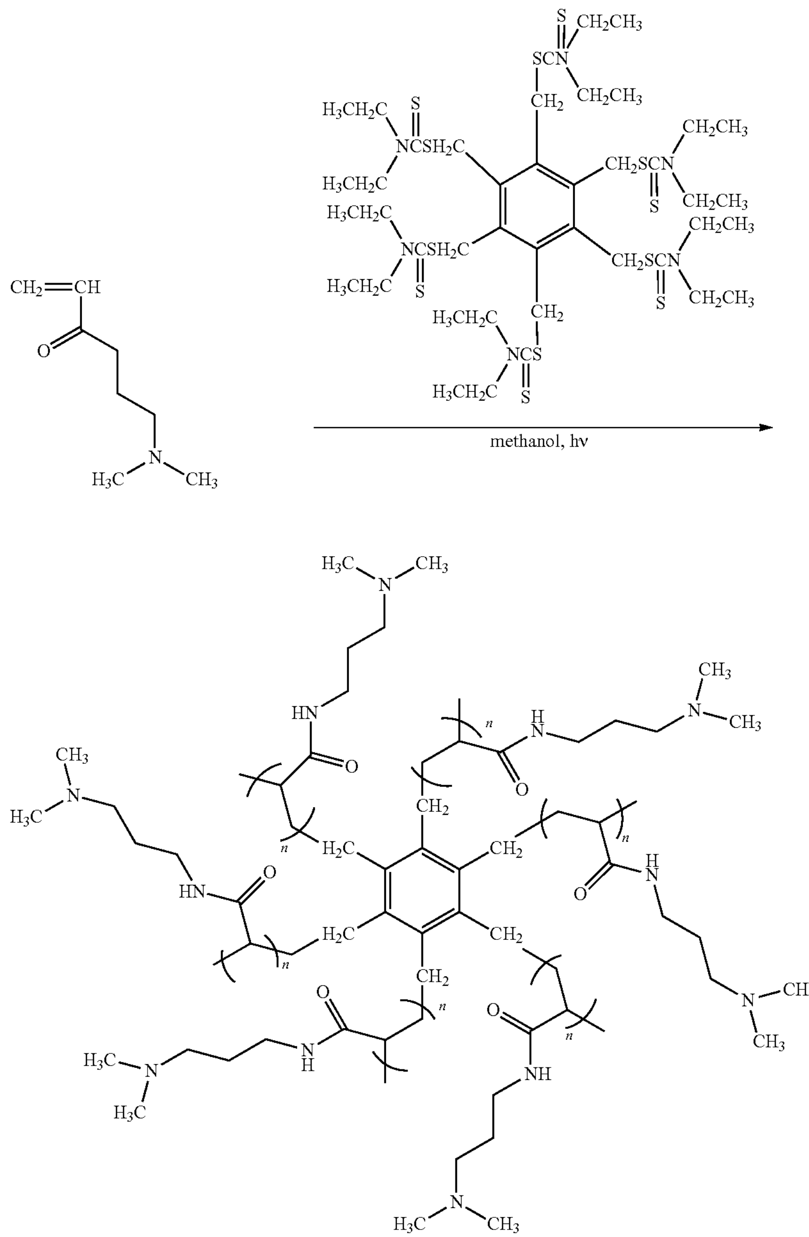

More specifically, hexakis (N,N-diethyldithiocarbamylmethyl) benzene (17.43 mg, 0.83 mmol, Mw. 1045) was dissolved in a small amount of chloroform and was added to dimethylaminopropyl acrylamide (3.9 g, 24.96 mol, Mw. 156.23). The mixture was diluted with chloroform so as to prepare solution of 20 ml in total. The solution thus prepared was agitated while nitrogen gas was blown in, and was irradiated with ultraviolet light (light intensity 1 mW/$cm^2$). After 30 minutes of ultraviolet irradiation, polymer solution was concentrated using an evaporator, and was added dropwise to a large quantity of diethylether to precipitate high-molecularweight polymer. After supernatant liquid was removed by decantation, the high-molecular-weight polymer was dissolved in water and was freeze-dried. Molecular weight of the high-molecular-weight polymer thus obtained was measured using a GPC after freeze-dried and was approximately 18,000. In addition, $^1$H-NMR: δ7.8 ppm to 7.4 ppm (br, 1H, —NH), δ3.43 to 3.0 ppm (br, 2H, —NH—$CH_2$—$CH_2$—), δ2.4 ppm to 2.2 ppm (br, 2H, —$CH_2$—$CH_2$—$NR_2$), δ2.2 ppm to 2.1 ppm (br, 6H, —N—$CH_3$), δ1.8 ppm to 1.5 ppm (br, 2H, —$CH_2$—$CH_2$—$CH_2$—).

(Formation of Nucleic-Acid-Containing Complex)

Each vector (2.36 mg, M.w. 18,000) was dissolved in tris-HCl-buffer (2 ml). 50 μL of solution thus obtained was taken and was diluted by adding tris-HCl-buffer so as to prepare vector solution of 500 μl in total. Separately, 2× buffer solution (450 μl) was added to pGL3 control plasmid so as to prepare DNA solution of 540 μl in total. The vector solution (67 μl) was added to the DNA solution (100 μl) (the ratio of the positive charge quantity of cationic high-molecular-weight polymer to the negative charge quantity of DNA was 1:1) and was left at rest for 24 hours at 37° C., thereby forming a nucleic-acid-containing complex. Particle size of polyion complex was measured by dynamic light scattering measurement and the result is shown in FIG. 1. In addition, changes of the average particle size with time are shown in FIG. 2.

Figure 2:
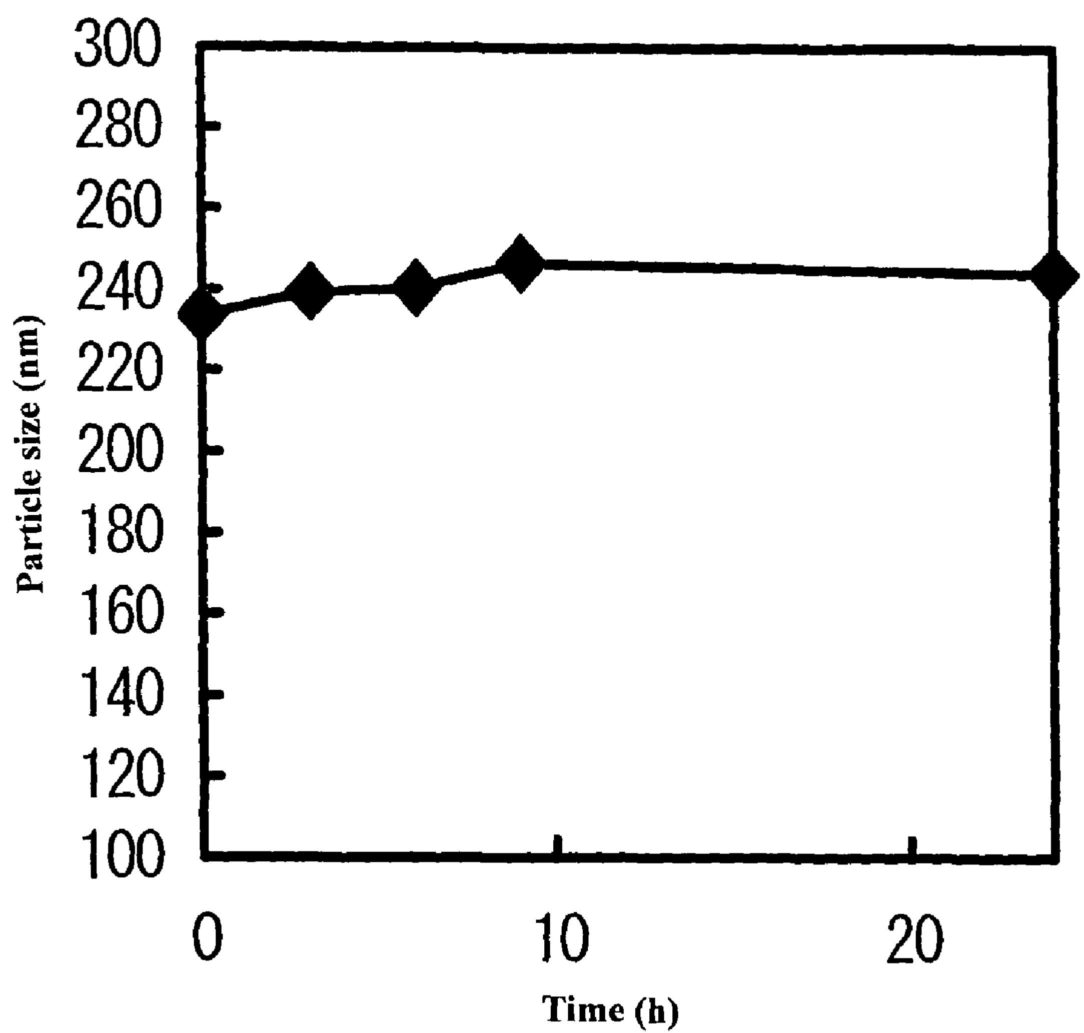
FIG. 2 is a graph showing changes with time in particle size of the polyion complex.

As shown in FIGS. 1 and 2, each cationic high-molecular-weight polymer formed a polyion complex immediately after mixed with the DNA. According to the result of cumulant analysis, it was found that nano-sized particles of approximately 250 nm were obtained and were still stable after 24 hours.

Polyion complex solution was added at a rate of 25 μl per well to COS-1 cells which has been incubated for a day on a 24 well-plate. The cells were incubated in a 5% $CO_2$ incubator. After 3 hours of incubation, the medium was removed and the cells were washed with PBS. After that, DMEM was added at a rate of 1 ml per well to the cells and the cells were incubated within the 5% $CO_2$ incubator again. After two days of incubation, the medium was removed and the cells were washed with PBS. After that, Luciferase cell culture lysis 5× Reagent was added at a rate of 200 μl per well and was left at rest. After 30 minutes, the cells were put into an Eppendorf tube and were centrifuged (4° C., 15,000 rpm, 1 min.). After centrifugation, each 4 μl of supernatant was collected onto a microplate and luciferase activity was measured using a luminometer. Moreover, 5 μL of supernatant after centrifugation was collected, and protein concentration determination was operated.

Figure 3:
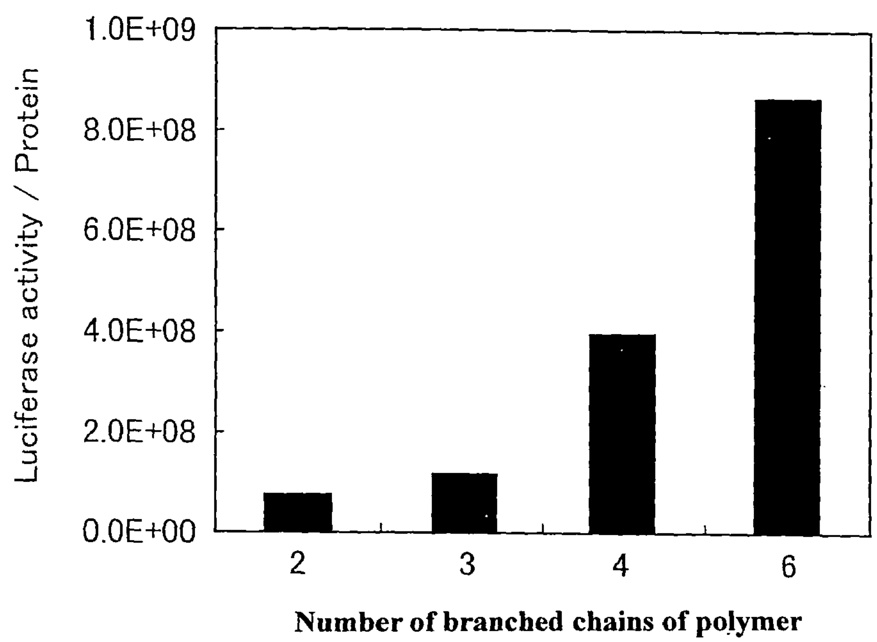
FIG. 3 is a graph showing results of transfection experiments.
Figure 4:
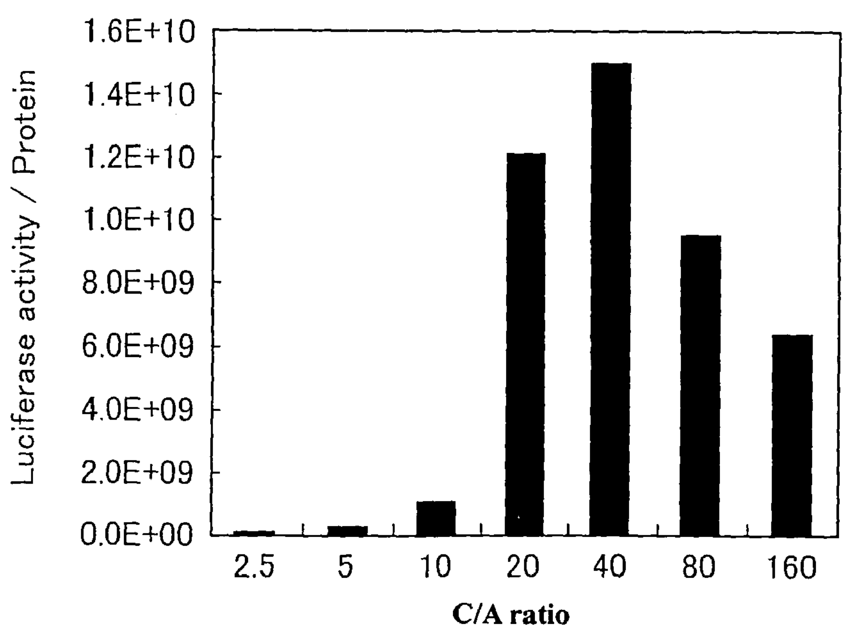
FIG. 4 is a graph showing measurement results of the relation between the cation/anion ratio and the gene expression efficiency.

Transfection experiments were conducted using high-molecular-weight polymer vectors having different numbers of branched chains. When C/A ratio was 10, the gene expression efficiency increased significantly as the number of the branched chains of the high-molecular-weight polymer increased as shown in FIG. 3. Effect on gene expression efficiency according to variation of the C/A ratio (cation/anion ratio) was also examined using a 6-branched-chain-type cationic high-molecular-weight polymer which exhibited the highest gene expression efficiency in the above experiments. As shown in FIG. 4, the highest gene expression efficiency was obtained when C/A=40.

As mentioned above, the present invention provides a vector which can make nucleic acids to be an aggregate and locate a vector containing a cationic polymer to surround the aggregate so as to protect the nucleic acids from the enzyme.

Figure 5:
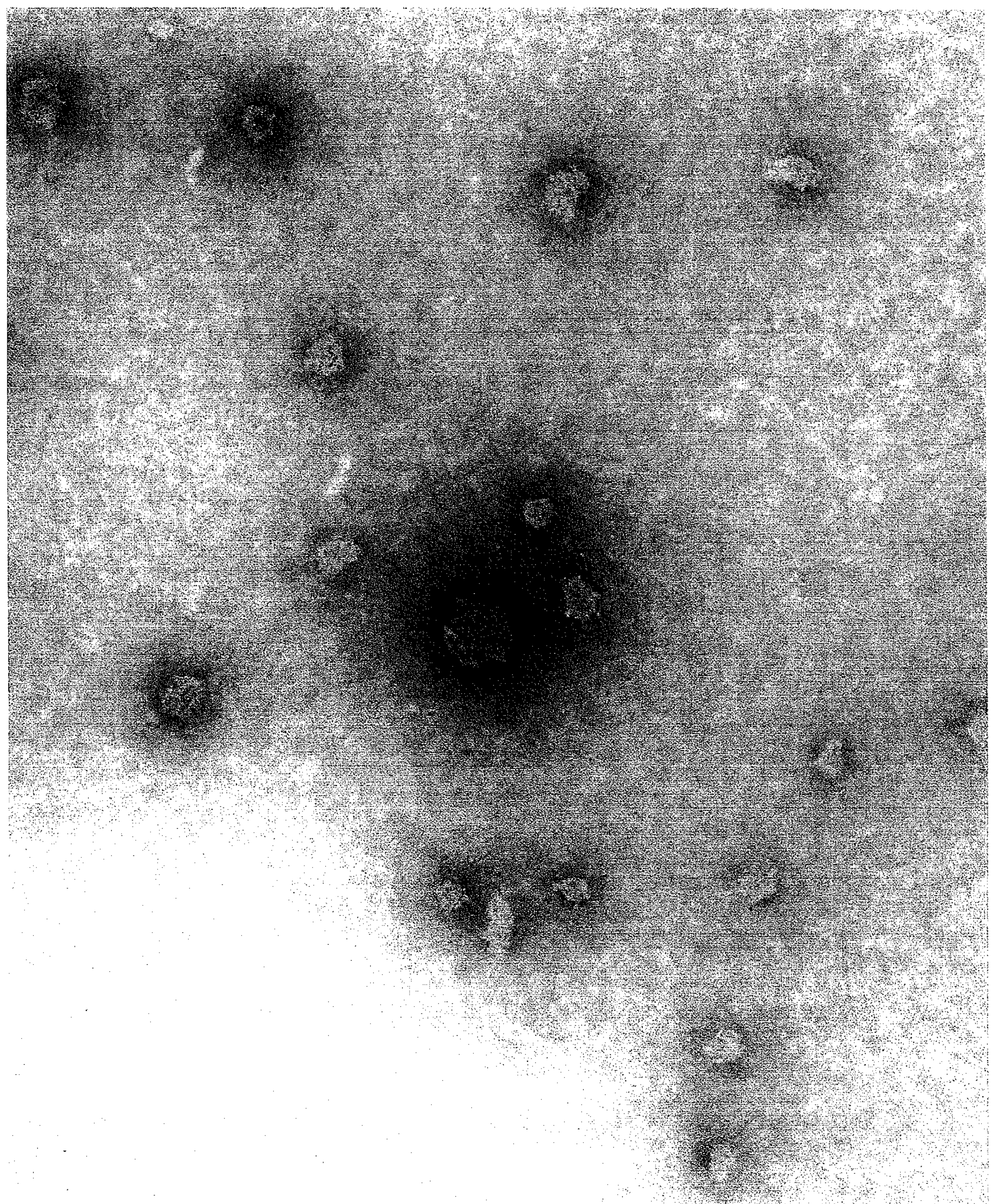
FIG. 5 is a TEM photograph of a gene complex, which is stained with phosphotungstic acid.
Figure 6:
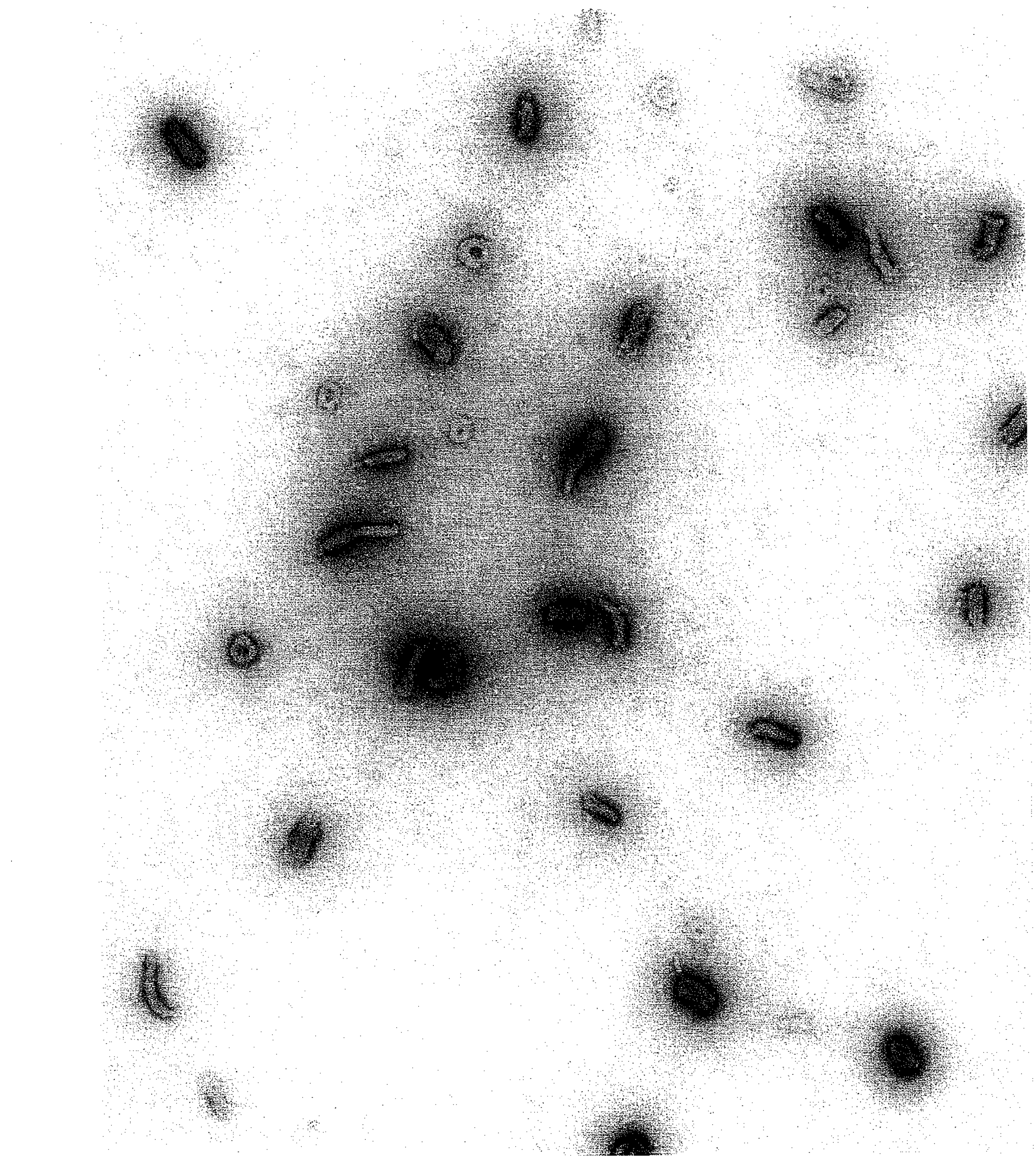
FIG. 6 is a TEM photograph of a gene complex, which is stained with uranium acetate.

FIGS. 5 and 6 are TEM photographs of gene complexes, each of which is a mixture of PGL3 plasmid and the aforementioned 6-branched-chain-type vector, wherein FIG. 5 shows a gene complex which is stained with phosphotungstic acid and FIG. 6 shows a gene complex which is stained with uranium acetate.

Figure 7:
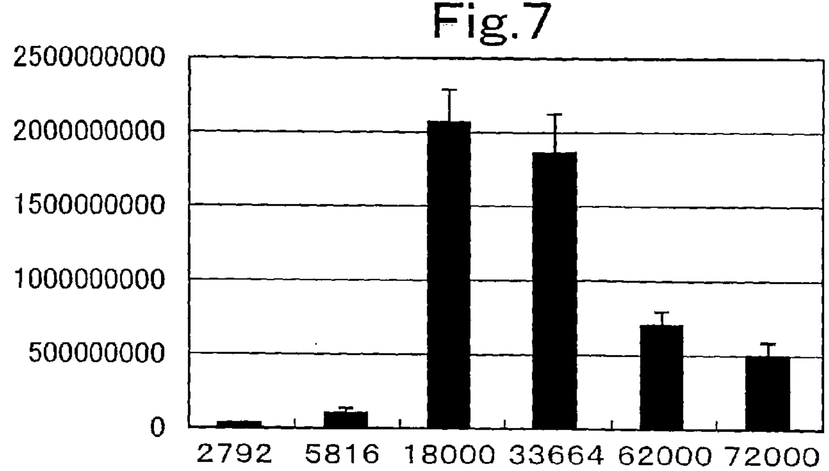
FIG. 7 is a graph showing the relation between the molecular weight of a vector having a single branched chain and the gene expression efficiency.

FIG. 7 is a graph showing the relation between the molecular weight of a vector having a single branched chain and the gene expression efficiency.

Figure 8:
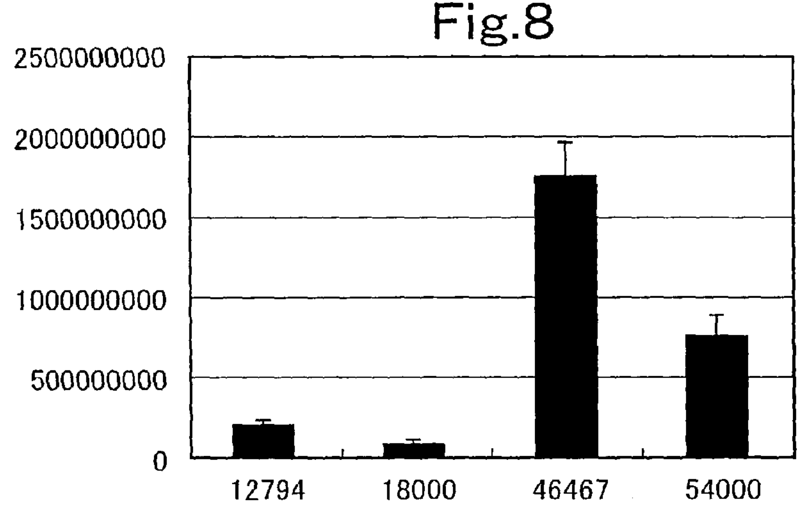
FIG. 8 is a graph showing the relation between the molecular weight of a vector having three branched chains and the gene expression efficiency.

FIG. 8 is a graph showing the relation between the molecular weight of a vector having three branched chains and the gene expression efficiency.

Figure 9:
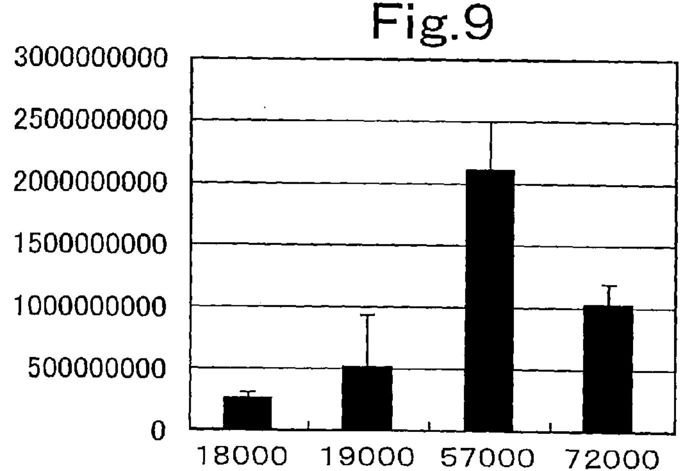
FIG. 9 is a graph showing the relation between the molecular weight of a vector having four branched chains and the gene expression efficiency.

FIG. 9 is a graph showing the relation between the molecular weight of a vector having four branched chains and the gene expression efficiency.

Figure 10:
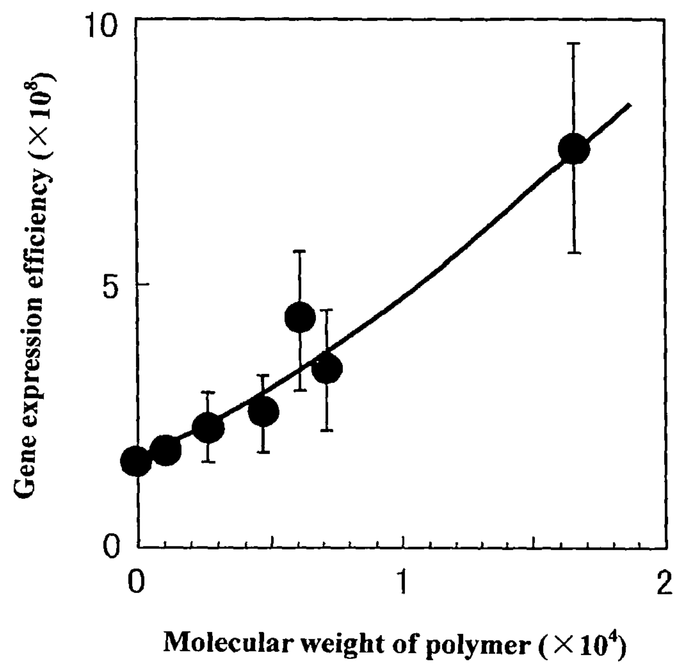
FIG. 10 is a graph showing the relation between the molecular weight of a block polymer and the gene expression efficiency, wherein the block polymer is a vector having four branched chains and a molecular weight of 10,000 and is prepared by block polymerizing dimethylacrylamide on ends of the branched chains.
Figure 11:
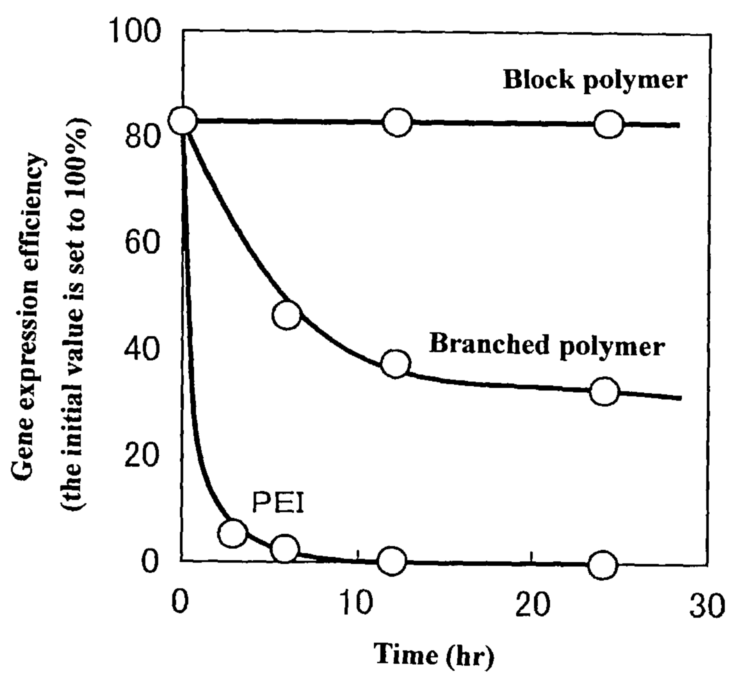
FIG. 11 is a graph showing the stability within the solution (changes with time when the initial value of the gene expression efficiency is set to 100%) of a block polymer of the vector, a branched polymer, and a PEI.

FIG. 10 is a graph showing the relation between the molecular weight of a block polymer and the gene expression efficiency, wherein the block polymer is a vector having four branched chains and a molecular weight of 10,000 and is prepared by block polymerizing dimethylacrylamide on ends of the branched chains, and FIG. 11 is a graph showing the stability within the solution (changes with time when the initial value of the gene expression efficiency is set to 100%) of a block polymer of the vector, a branched polymer, and a PEI.

What is claimed is:

1. A nucleic-acid-containing complex comprising a nucleic acid and a vector, wherein the vector is represented by a Formula selected from the group consisting of Formula (I) and Formula (II):

Formula (I)

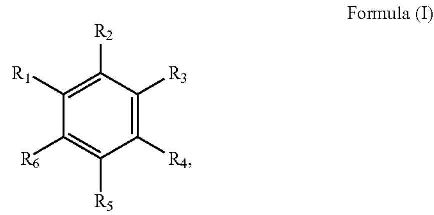

wherein $R_1$-$R_6$ each represent polymer chains, wherein $R_1$-$R_6$ may each be the same or different, Formula (II)

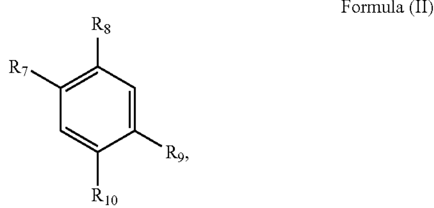

wherein $R_7$-$R_{10}$ each represent polymer chains, wherein $R_7$-$R_{10}$ may each be the same or different, wherein the polymer chains represented by $R_1$-$R_{10}$ are polymers consisting of dimethylaminopropyl acrylamide monomers, and wherein said nucleic-acid-containing complex has a particle size of about 50 to about 400 nm.

2. The nucleic-acid-containing complex of claim 1, wherein the vector is of Formula II and has a molecular weight of from 30,000 to 65,000.

3. The nucleic-acid-containing complex of claim 1, wherein the vector is of Formula I and has a molecular weight of from 10,000 to 50,000.

4. A nucleic-acid-containing complex as claimed in claim 1, wherein said vector is represented by Formula (I).

5. The nucleic-acid-containing complex of claim 1, wherein the molecular weight of the vector is from 5,000 to 500,000.

6. The nucleic-acid-containing complex of claim 1, wherein the molecular weight of the vector is from 5,000 to 50,000.

7. The nucleic-acid-containing complex as claimed in claim 1, wherein said nucleic-acid-containing complex has a particle size of approximately 250 nm, wherein a cation/anion ratio of said nucleic-acid-containing complex is 20 to 160, and wherein the vector is represented by Formula (I) and has a molecular weight of approximately 18,000.

* * * * *